United States Patent [19]

Engelman et al.

[11] Patent Number: 5,739,273
[45] Date of Patent: Apr. 14, 1998

[54] TRANSMEMBRANE POLYPEPTIDE AND METHODS OF USE

[75] Inventors: Donald M. Engelman, Guilford, Conn.; John F. Hunt, Dallas, Tex.

[73] Assignee: Yale University, New Heaven, Conn.

[21] Appl. No.: 303,651

[22] Filed: Sep. 9, 1994

Related U.S. Application Data

[63] Continuation of Ser. No. 835,707, Feb. 12, 1992, abandoned.
[51] Int. Cl.[6] .......................... A61K 38/00; A61K 38/02; C07K 5/00; C07K 7/00
[52] U.S. Cl. .......................... 530/324; 530/324; 530/326
[58] Field of Search .............................. 514/12; 530/324, 530/325, 326

[56] References Cited

PUBLICATIONS

Popot et al, Biochemistry, vol. 29, No. 17, 1990, pp. 4031–4037.
Danshina et al., Ach. Biochem. Biophys. vol. 279, No. 2, Jun. 1990, pp. 225–231.
Bormann, B.J. and D.M. Engelman, "Intramembrane Helix–Helix Association in Oligomerization and Trasnmembrane Signaling," Annu. Rev. Biophys. Biomol. Struct. 21:223–243 (1992).
Abrams, et al., "Identification of Translocated Gating Charge in a Voltage–dependent Channel," J. Gen. Physiol. 98:77–93 (1991).
Briggs, et al., "Conformations of Signal Peptides Induced by Lipids Suggest Initial Steps in Protein Export," Science, vol. 233, pp. 206–208 (Jul. 1986).
Briggs, et al., "In Vivo Function and Membrane Binding Properties Are Correlated for Escherichia coli LamB Signal Peptides," Science, vol. 288, pp. 1096–1098 (May 31, 1985).
Cornell, et al., "Conformations and Orientations of a Signal Peptide Interacting with Phospholipid Monolayers," Biochemistry, vol. 28, No. 7, pp. 2789–2797 (1989).
Engelman, et al., "The Spontaneous Insertion of Proteins into and across Membranes: The Helical Hairpin Hypothesis," Cell 23:411–422 (1981).
Engelman et al., "Identifying Nonpolar Transbilayer Helices in Amino Acid Sequences of Membrane Proteins," Ann. Rev. Biophys. Chem. 15:321–353 (1986).
Geller, et al., M13 Procoat Inserts into Liposomes in the Absence of Other Membrane Proteins, The Journal of Biological Chemistry, vol. 260, No. 24, pp. 13281–13285 (Oct. 25, 1985)
Goormaghtiah, et al., "Secondary Structure and Orientation of the Amphipathic Peptide GALA in Lipid Structures. An Infrared–Spectroscopic Approach" European Journal of Biochemistry, vol. 195, No. 1, pp. 421–429 (Jan. 1, 1991).

Hoch, et al., "Channels Formed by Botulinum, Tetanus, and Diphtheria Toxins in Planar Lipid Bilayers: Relevance to Translocation of Proteins Across Membranes," Proc. Nat. Acad. Sci. 82:1692–1696 (1985).
Hunt, et al., "Biophysical Studies of the Integral Membrane Protein Folding Pathway," Biophysical Journal Program and Abstracts, 35th Annual Meeting, Moscone Center, San Francisco, California, Abstract No. W–AM–K2 (Feb. 24–28, 1991).
McKnight, et al., "Fluorescence Analysis of Tryptophan–Containing Variants of the LamB Signal Sequence upon insertion into a Lipid Bilayer," Biochemistry, vol. 30, No. 25, pp. 6241–6246 (1991).
McKnight, et al., "Functional and Nonfunctional LamB Signal Sequence Can Be Distinguished by Their Biophysical Properties," The Journal of Biological Chemistry, vol. 264, No. 29, pp. 17293–17297 (Oct. 15, 1989).
Neville, et al., "Transmembrane Transport of Diphtheria Toxin, Related Toxins, and Colicines," Ann. Rev. Biochem. 55:195–224 (1986).
Parente, et al., "Association of pH–Sensitive Peptide with Membrane Vesicles: Rose of Amino Acid Sequence," Biochemistry, vol. 29, No. 37, pp. 8713–8719 (1990).
Parente, et al., "pH–dependent Fusion of Phosphatidylcholine Small Vesicles," The Journal of Biological Chemistry, vol. 263, No. 10, pp. 4724–4730 (Apr. 5, 1988).
Song, et al., "Membrane Topography of ColE1 Gene Products: the Hydrophobic Anchor of the Colicin E1 Channel is a Helical Hairpin," J. Bacteriol. 173:2927–2934 (1991).
Subbarao, et al., "pH–Dependent Bilayer Destabilization by an Amphipathic Peptide," Biochemistry, vol. 26, No. 11, 2964–2972 (1987).
Von Heijne, G. "Signal Sequences are not Uniformly Hydrophobic," Journal of Molecular Biology, vol. 159, No. 4, pp. 537–541 (Aug. 25, 1982).
Wickner, W., "Assembly of Proteins into Membranes," Science 210:861–868 (1980).
Wolfe, et al., "Effects of Two sec Genes on Protein Assembly into the Plasma Membrane of Escherichia coli," The Journal of Biological Chemistry, vol. 260, No. 3, pp. 1836–1841 (Feb. 10, 1985).

Primary Examiner—Avis M. Davenport
Attorney, Agent, or Firm—Arnall Golden & Gregory, LLP

[57] ABSTRACT

A water-soluble polypeptide having the characteristics of the bacteriorhodopsin C helix such that it is largely hydrophobic and spontaneously inserts into a biological membrane as an alpha-helix. The polypeptide is administered as an aqueous solution or is contained within the lipid bilayer of a liposome. The polypeptide is modified so that it will interfere with the helix—helix interactions within the membranes of adverse cells or is coupled to a therapeutic substance, such as a protein or pharmaceutical compound, for transmission thereof through the membrane and into the cell.

10 Claims, 6 Drawing Sheets

TRANSMEMBRANE POLYPEPTIDE AND METHODS OF USE

PRIORITY INFORMATION

This application is a continuation under 37 C.F.R. §1.60 of U.S. Ser. No. 07/835,707, filed Feb. 12, 1992 and now abandoned.

The United States government has rights in this invention by virtue of grant numbers 5 P01 GM 39546-05 from the National Institutes of Health and DMB-8805587 from the National Science Foundation.

BACKGROUND OF THE INVENTION

The present invention relates to the field of protein biochemistry and more particularly relates to a transmembrane polypeptide.

A therapeutic substance such as a protein or a pharmaceutical compound must move from the site of administration through numerous cells and tissues to the site of action. In order for a molecule to pass through or into a cell, it must first penetrate the cell membrane.

Cell Membranes

Cell membranes are composed mainly of phospholipids and proteins, both containing hydrophobic and hydrophilic groups. The lipids orient themselves into an orderly bilayer configuration within the membrane core with the hydrophobic chains facing toward the center of the membrane while the hydrophilic portions are oriented toward the outer and inner membrane surfaces. The proteins are dispersed throughout the lipid layer, in some instances protruding through the surface of the membrane or extending from one side of the membrane to the other with some of the hydrophobic residues being buried in the interior of the lipid bilayer.

The barrier action of the membrane often restricts and sometimes even prevents the passive penetration of many substances through the membrane into or out of the cell. However, it is known that the proteins integrated across the lipid bilayer transmit information from the exterior to the interior of the cell.

Therefore, a mechanism is needed to facilitate or enable the passage of substances such as pharmaceutical drugs, chemicals or proteins across cell membranes.

Helix—helix Interactions

Popot and Engelman, *Biochem.* 29:4031–4037 (1990), recently proposed a two-stage model of helix formation for transmembrane proteins in which the alpha-helices first insert into the lipid bilayer and then assemble into a tertiary structure that includes interactions with other intramembrane alpha-helices of the protein or with alpha-helices of other polypeptides in the membrane.

Signal transduction, or the transmission of a signal to the interior of the cell indicating an event on the surface of the cell, may be achieved by interactions of these transmembrane alpha-helices. Any interference with transmembrane alpha-helical interactions might interrupt the signal. Interruption of a signal that confers an adverse effect, such as the unregulated proliferation of a cancer cell or maturation of a viral cell, could result in a beneficial effect.

It is therefore an object of the present invention to provide a compound that can insert into the lipid bilayer of the membrane of a deleterious cell or virus, and interferes with the signal transduction of that cell or virus.

It is a further object of the present invention to provide a method of inhibiting cancer cell proliferation.

It is a further object of the present invention to provide a method of inhibiting viral cell maturation.

It is a further object of the present invention to provide a method of delivering a therapeutic agent across a cell membrane.

SUMMARY OF THE INVENTION

A water-soluble, hydrophobic polypeptide that spontaneously inserts into a cell membrane is provided. The polypeptide is used to inhibit proliferation or maturation of undesirable cells such as cancer or virally-infected cells by interfering with the helix—helix interactions within the membranes of these cells or is coupled to a therapeutic agent, such as a protein or pharmaceutical compound, for transmission thereof through the membrane and into the cell.

The polypeptide is either synthesized or isolated from the bacteriorhodopsin and corresponds to the C helix in the primary structure. The synthetic polypeptide maintains the characteristics of the bacteriorhodopsin C helix by including a hydrophobic alpha-helical transmembrane region containing one or more acidic or basic amino acids. Preferably, the amino acids are aspartic acid, glutamic acid, lysine, arginine or histidine.

The polypeptide is preferably coupled to a pharmaceutical compound by a sulfhydryl or disulfide bond via a cysteine residue included in the non-helical portion of the molecule. The polypeptide is attached to a therapeutic protein or polypeptide by synthetically extending the polypeptide sequence to include the therapeutic sequence. Alternatively, a side chain of an amino acid in the helical portion of the polypeptide is modified in such a way that it interacts with other alpha-helices within the membrane to prevent or inhibit cell proliferation or maturation.

The polypeptide is administered in an aqueous solution, is incorporated into the lipid bilayer of a liposome or is in the form of a lipoprotein particle.

The specificity of the polypeptide for a particular cell type is enhanced by attaching a target molecule such as a ligand or receptor either directly to the polypeptide or within the lipid bilayer of a liposome containing the polypeptide.

DETAILED DESCRIPTION OF THE INVENTION

A polypeptide derived from the bacteriorhodopsin C helix sequence has been identified that is both water-soluble and largely hydrophobic so that it spontaneously inserts into the lipid bilayer of a biological membrane. The isolated polypeptide, or a synthetic polypeptide having the characteristics of the isolated polypeptide, are useful therapeutic agents for the treatment of a cellular disease or disorder. The polypeptide is soluble at neutral pH in aqueous buffers free of both detergents and aqueous phase perturbants such as urea. The polypeptide spontaneously inserts itself into the membrane of a target cell to either disrupt the metabolism of an adverse cell or to transmit a therapeutic agent, such as a protein or pharmaceutical compound through the membrane into the cytoplasm of the cell requiring therapy.

The term bacteriorhodopsin C molecule is defined herein as any molecule homologous to the bacteriorhodopsin C molecule. A homologous bacteriorhodopsin C molecule is one that is water-soluble, largely hydrophobic and capable of spontaneously inserting itself into a lipid bilayer as an alpha-helix.

Amino Acid Sequence

The polypeptide includes the amino acid sequence of the C helix of bacteriorhodopsin from *Halobacterium halobium* or an amino acid sequence maintaining the characteristics of the bacteriorhodopsin C molecule, namely a polypeptide that is water-soluble, largely hydrophobic, and spontaneously changes its extended conformation to form an alpha-helix that inserts into the lipid bilayer of a biological membrane. The polypeptide is either isolated from the bacteriorhodopsin molecule of *H. halobium* or a mutant thereof by conventional methods or is synthesized by techniques well known to those skilled in the art based on the amino acid sequence of the isolated bacteriorhodopsin C helix. Specific alterations of the amino acid sequence can be made to achieve the desired biological activity while retaining the properties of solubility and spontaneous insertion.

The macromolecular assembly of the bacteriorhodopsin molecule includes one polypeptide which contain a total of seven alpha-helical transmembrane segments as described in the paper of Engelman et al., *Ann. Rev. Biophys. Chem.* 15:321–353 (1986). These helices have been assigned the letters A through G with the helix designated "A" proximal to the amino terminal of the molecule. Each helix contains approximately 20 hydrophobic and uncharged amino acids. The amino acid sequence of all seven regions of the bacteriorhodopsin molecule is shown below and is set forth in the sequence listing as sequence identification number 2. The seven underlined regions of the amino acid sequence below correspond to the seven alpha-helical transmembrane domains. The amino acid sequence corresponding to the bacteriorhodopsin C molecule is shown below in bold.

| GLU | ALA | GLN | ILE | THR | GLY | ARG | PRO | GLU | TRP | ILE | TRP | LEU | ALA | LEU | GLY |
|---|---|---|---|---|---|---|---|---|---|---|---|---|---|---|---|
| THR | ALA | LEU | MET | GLY | LEU | GLY | THR | LEU | TYR | PHE | LEU | VAL | LYS | GLY | MET |
| GLY | VAL | SER | ASP | PRO | ASP | ALA | LYS | LYS | PHE | TYR | ALA | ILE | THR | THR | LEU |
| VAL | PRO | ALA | ILE | ALA | PHE | THR | MET | TYR | LEU | SER | MET | LEU | LEU | GLY | TYR |
| GLY | LEU | THR | MET | VAL | PRO | PHE | GLY | GLY | GLU | GLN | ASN | PRO | ILE | TYR | TRP |
| ALA | ARG | TYR | ALA | ASP | TRP | LEU | PHE | THR | THR | PRO | LEU | LEU | LEU | LEU | ASP |
| LEU | ALA | LEU | LEU | VAL | ASP | ALA | ASP | GLN | GLY | THR | ILE | LEU | ALA | LEU | VAL |
| GLY | ALA | ASP | GLY | ILE | MET | ILE | GLY | THR | GLY | LEU | VAL | GLY | ALA | LEU | THR |
| LYS | VAL | TYR | SER | TYR | ARG | PHE | VAL | TRP | TRP | ALA | ILE | SER | THR | ALA | ALA |
| MET | LEU | TYR | ILE | LEU | TYR | VAL | LEU | PHE | PHE | GLY | PHE | THR | SER | LYS | ALA |
| GLU | SER | MET | ARG | PRO | GLU | VAL | ALA | SER | THR | PHE | LYS | VAL | LEU | ARG | ASN |
| VAL | THR | VAL | VAL | LEU | TRP | SER | ALA | TYR | PRO | VAL | VAL | TRP | LEU | ILE | GLY |

| | | | | | | | | | | | | | | |
|---|---|---|---|---|---|---|---|---|---|---|---|---|---|---|
| SER | GLU | GLY | ALA | GLY | ILE | VAL | PRO | LEU | ASN | ILE | GLU | THR | LEU | LEU | PHE |
| MET | VAL | LEU | ASP | VAL | SER | ALA | LYS | VAL | GLY | PHE | GLY | LEU | ILE | LEU | LEU |
| ARG | SER | ARG | ALA | ILE | PHE | GLY | GLU | ALA | GLU | ALA | PRO | GLU | PRO | SER | ALA |
| GLY | ASP | GLY | ALA | ALA | ALA | THR | SER | | | | | | | | |

The synthetic polypeptide need not have an amino acid sequence identical to the amino acid sequence of the isolated bacteriorhodopsin C molecule polypeptide shown above in bold, but should include a hydrophobic segment of approximately 20 amino acids that forms an alpha-helix capable of spanning the lipid bilayer and includes at least one acidic or basic amino acid within the alpha-helical region that can be titrated upon changing the pH. The titratable amino acid is preferably one that having a charged side chain such as aspartic acid, glutamic acid, lysine, arginine or histidine. Most preferably, the titratable amino acid is aspartic acid.

At a slightly basic pH, the polypeptide having the characteristics of the bacteriorhodopsin C molecule is soluble, non-helical and does not insert into the membrane. As the pH is lowered the polypeptide changes its conformation to an alpha-helix and spontaneously inserts into the lipid bilayer of the cell membrane. The pKa for insertion of the polypeptide is preferably 6.0 so that at a neutral pH approximately 10% of the polypeptide molecules are inserted into the membrane while 90% are peripherally associated with the membrane, but not inserted. It is believed that the conformational change from linear to alpha-helix is due to protonation of the acidic amino acids within the alpha-helical region upon exposure of the polypeptide to the increased hydrogen ion concentration.

Figure 1:
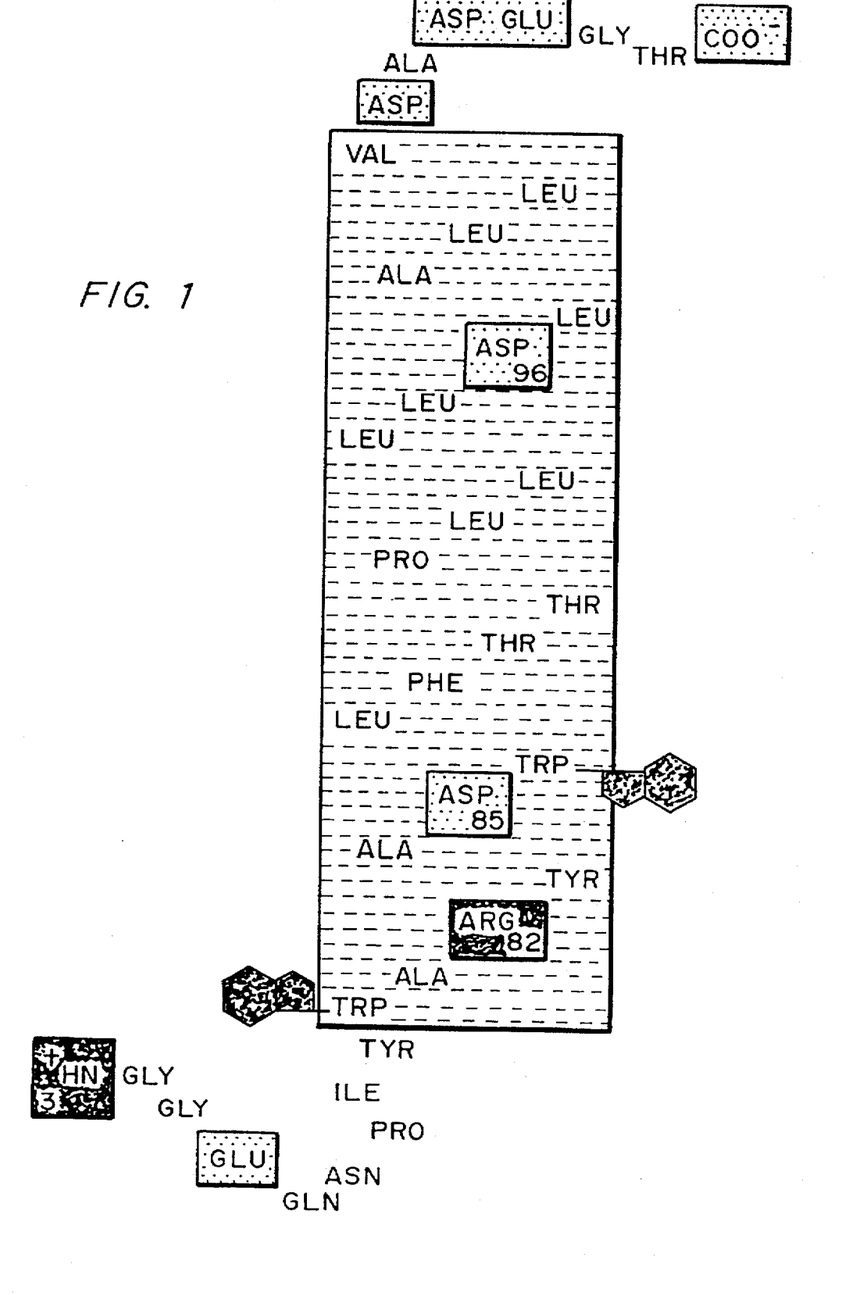
FIG. 1 is a schematic representation of a synthetic polypeptide corresponding to the bacteriorhodopsin C helix wherein glutamine, located three amino acids from the carboxy terminal, is replaced with glutamic acid. The large grey rectangle indicates the alpha-helical portion of the molecule inserted within a cell membrane. The light grey boxes indicate acidic groups while the black boxes indicate basic groups.
Figure 2:
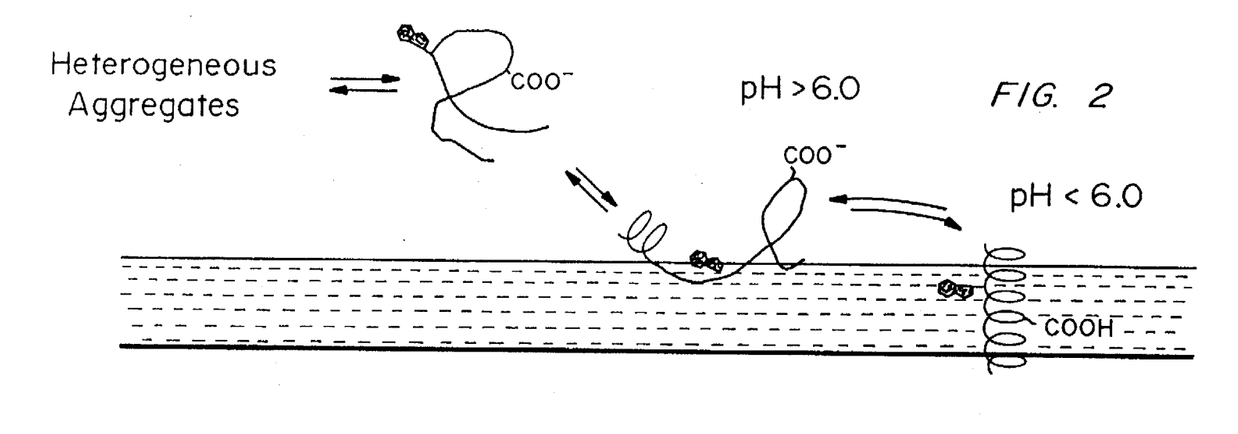
FIG. 2 is a schematic representation of the water-soluble hydrophobic polypeptide showing the conformational change of the polypeptide from an extended molecule to an alpha-helix for insertion into the biological membrane of a cell. The grey region represent a cell membrane. The black chemical ring structure is the side group of the tryptophan molecule The titratable amino acid is shown as COO— in the extended molecule and COOH in the alpha-helical molecule.

The amino acid sequence of a preferred synthetic polypeptide is shown schematically in FIG. 1 and as sequence identification number 1 in the attached sequence listing. This synthetic amino acid sequence differs from the amino acid sequence of the naturally occurring bacteriorhodopsin molecule by the substitution of a glutamic acid residue for the glutamine residue located at amino acid position 34 in the bacteriorhodopsin C peptide sequence. The alpha-helical portion of the polypeptide begins at the ninth amino acid from the amino terminal (tryptophan) and ends at the thirtieth amino acid (valine). The non-helical portions extend below and above the membrane as shown in FIGS. 1 and 2.

Modification of Side Chains

As described above, the polypeptide can be used therapeutically to interfere with helix—helix interactions of proteins located within the membrane of adverse entities such as cancer or enveloped viruses. There is strong evidence supporting the theory that unregulated cell proliferation is due to the presence of an oncogene encoding a transmembrane protein similar to a growth factor receptor but unresponsive to cellular control. For example, the herd-2 or neu oncogene encodes an epidermal growth factor receptor-like membrane protein that causes a loss of cell growth control. The epidermal growth factor receptor contains an alpha-helical transmembrane region that is believed to interact with other helices to regulate cell growth. The protein encoded by the neu oncogene contains a single amino acid change in the amino acid sequence that either prevents the helix—helix interactions essential for cell regulation or causes an adverse helix—helix interaction that prevents control of cell proliferation.

Administration of a water-soluble hydrophobic polypeptide that either competes with the protein encoded by an oncogene for interactions with the cell-regulating transmembrane protein or interrupts interactions between the alpha-helix of the oncogene-encoded protein and other alpha-helices would beneficially modulate receptor function and allow control of cell proliferation. The amino acid sequence of such a polypeptide is determined by examining differences between the oncogene-encoded transmembrane polypeptides and the normal growth factor receptor transmembrane polypeptides. The water-soluble hydrophobic polypeptide is then modified to include a sequence of amino acids having side chains that facilitate this type of desired helix—helix interaction.

The water-soluble hydrophobic polypeptide can also be administered to an individual infected with a virus to prevent or inhibit maturation of the virus, such as human immunodeficiency virus (HIV), by either competing with viral transmembrane proteins for helix—helix interactions or otherwise interrupting helix—helix interaction between proximal viral membrane proteins.

Attachment of Protein

The water-soluble hydrophobic polypeptide is used therapeutically to transmit non-lipid soluble peptides through the cell membrane and into the cytoplasm of a cell by extending the synthetic sequence of the spontaneously inserting polypeptide to include the therapeutic sequence.

For example, a number of short, hydrophilic peptides have been identified that provide a therapeutic effect by inhibiting the intracellular HIV protease molecule. These hydrophilic therapeutic peptides can be delivered to the cytoplasm of an HIV-infected cell by attachment to the spontaneously inserting polypeptide as described above.

Attachment of Chemical Compounds

A membrane-impermeable pharmaceutical compound, or other therapeutic chemical, is attached to the water-soluble hydrophobic polypeptide by substituting one of the residues of the non-helical portion of the polypeptide, preferably a glycine or threonine residue, with an amino acid containing a free sulfhydryl such as cysteine, and then coupling the compound to the cysteine residue by a disulfide linkage. The compound is then transmitted through the membrane into the cytoplasm of the cell by the spontaneous insertion of the polypeptide as shown schematically in FIG. 3. The same goal is accomplished by utilizing alpha amino acids other than the twenty usually found in proteins. In addition, other chemical linkages known to those skilled in the art could be used to attach the compound to the polypeptide.

Attachment of a Target Molecule

Figure 3:
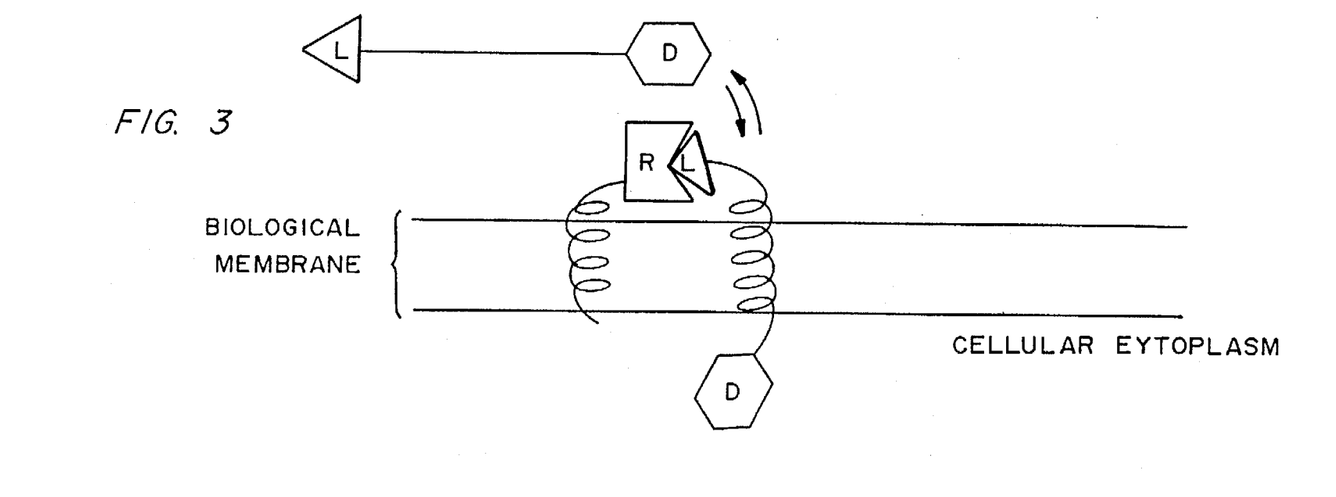
FIG. 3 is a schematic representation of the water-soluble hydrophobic polypeptide coupled to a drug and a targeting molecule showing the conformational change of the polypeptide from an extended molecule to an alpha-helix for insertion into the biological membrane of a cell. The letter "L" designates a ligand or targeting molecule, the letter "R" designates a receptor, and the letter "D" designates a drug.

The specificity of the water-soluble hydrophobic polypeptide for a particular type of cell is improved by attachment of a targeting molecule, such as an antibody or receptor molecule, to the polypeptide as shown in FIG. 3. A target protein molecule is attached by a peptide bond while a target chemical is attached by a sulfhydryl or disulfide bond as described above.

The targeting molecule can either be attached to the polypeptide as described above and shown in FIG. 3 or can be inserted into the membrane of a liposome containing the polypeptide and therapeutic agent as described in more detail below.

Liposome Delivery

Figure 4:
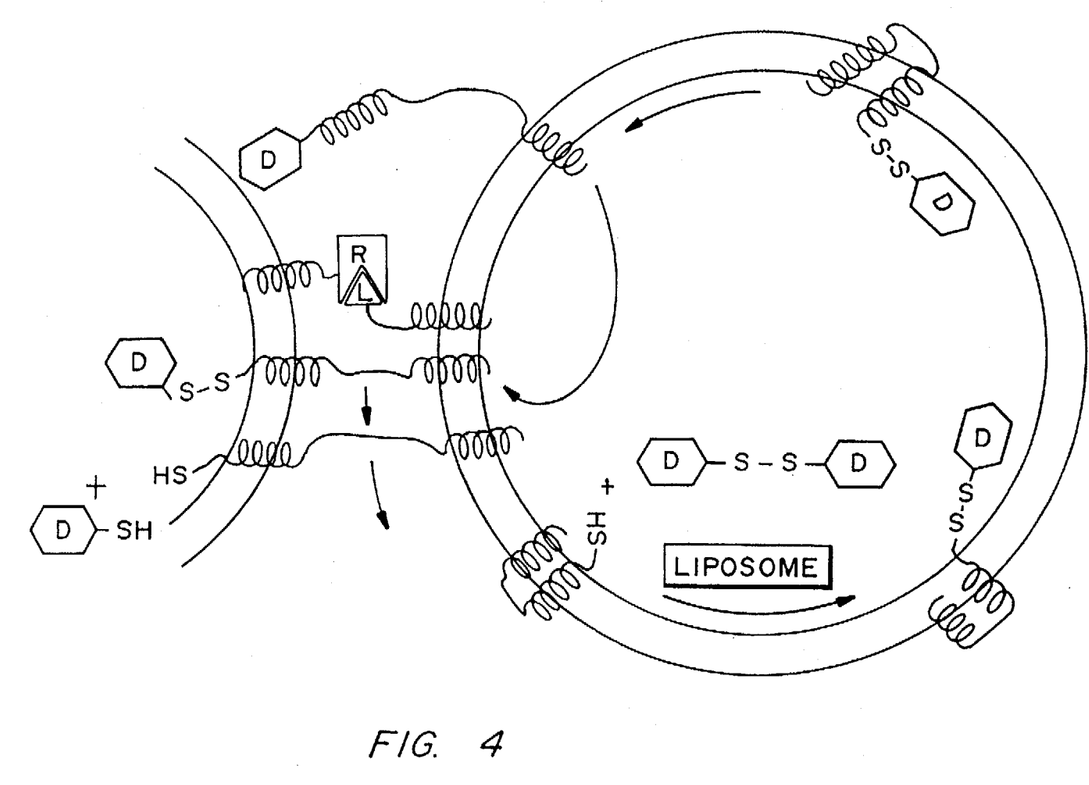
FIG. 4 is a schematic representation of the water-soluble hydrophobic polypeptide contained within a liposome using the letter designations specified above for FIG. 3.

As shown in FIG. 4, the water-soluble polypeptide can be inserted into a unilamellar phospholipid vesicle or liposome for delivery to the cell requiring therapy. Liposomes are formed from commercially available phospholipids supplied by a variety of vendors including Avanti Polar Lipids, Inc. (Birmingham, Ala.).

The liposome-associated polypeptide is prepared by mixing an aqueous solution of the polypeptide, prepared as described below, with reconstituted lipid vesicles. Preferably the lipid vesicles are reconstituted in a buffer solution containing approximately 20 mM sodium chloride and 5 mM sodium phosphate at an approximate pH of 8.0.

The liposome can include a ligand molecule specific for a receptor on the surface of the target cell to direct the liposome to the target cell as shown in FIG. 5.

If the polypeptide is used for the delivery of a pharmaceutical compound to a cell, the lumen of the liposome preferably can contain additional compound in solution for regeneration of uncoupled polypeptide as shown in FIG. 3.

Starting at the left side of the liposome shown in FIG. 3 and moving counter-clockwise, a ligand molecule on the liposome binds to a receptor molecule on the target cell to bring the liposome close together. A polypeptide coupled to the therapeutic compound or drug (D) exits the liposome and inserts itself into the membrane of the target cell, delivering the compound to the cytosol of the target cell. The polypeptide releases the compound and returns to the lipid membrane of the liposome. The membrane-inserted polypeptide couples to a second molecule of the compound (D) contained within the lumen of the liposome. The polypeptide exits the liposome and inserts into the membrane of the cell to deliver a second dose of the drug. The process continues until the reservoir of drug in the lumen of the liposome is exhausted.

Alternatively, the water-soluble polypeptide is delivered in the form of a lipoprotein particle.

Alpha-helical Conformation

The well-known spectroscopic technique of polarized infrared linear dichroism is used to determine the orientation of the alpha-helical domain of the polypeptide. The orientation of the polypeptide in protein/phospholipid multilayers is inferred from the dichroism of two amide vibrations.

Figure 5A:
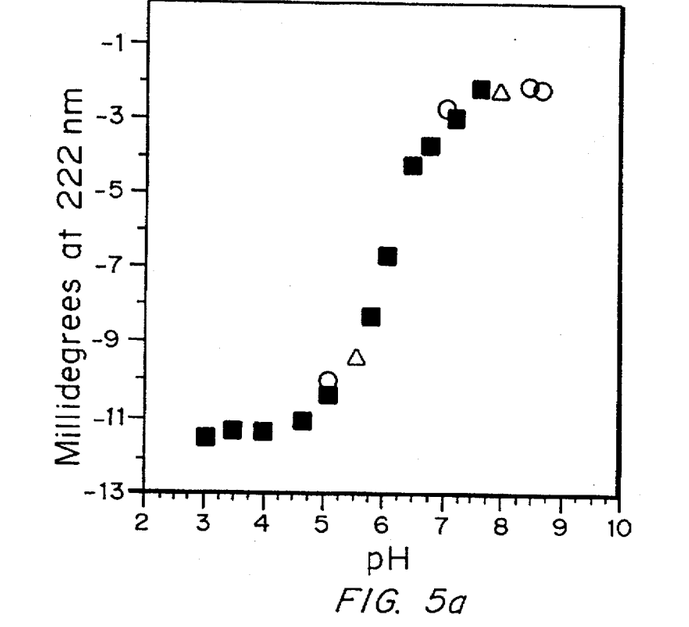
FIG. 5A is a graph showing the circular dichroism analysis of the synthetic polypeptide of FIG. 1 in the presence of dimyristoyl phosphatidylcholine (DMPC) vesicles at various pH values. The black squares indicate the initial titration (down). The open circles indicate the reverse titration (up). The open triangles indicate the second titration (down).
Figure 5B:
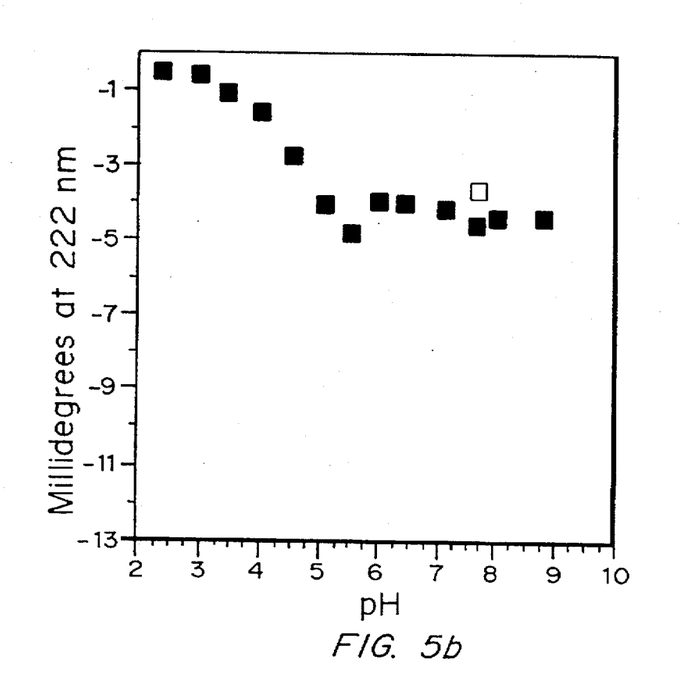
FIG. 5B is a graph showing the circular dichroism analysis of the synthetic polypeptide of FIG. 1 in the presence of lipid molecules. The symbols are the same as set forth in FIG. 5A.

FIG. 5A is a graph showing circular dichroism titration of the synthetic polypeptide having the amino acid sequence set forth in FIG. 1 and sequence listing identification number 1, in the presence of a solution containing small unilamellar phospholipid vesicles made from synthetic dimyristoyl phosphatidylcholine. The y axis is millidegrees at 222 nanometers, and the x axis is pH. This graph reveals the formation of a polypeptide alpha-helix with a pKa of pH 6.0. FIG. 5B is a corresponding control graph showing circular dichroism titration of the polypeptide in the presence of lipid molecules.

Orientation with Respect to Membrane

The well-known technique of Fourier Transform Infrared (FTIR) spectroscopy of macroscopically ordered protein/phospholipid multilayers is used to establish the orientation of the polypeptide relative to the lipid bilayer. The absence of signal in the regions corresponding to the amide residues of the peptide bond indicates a lack of peptide orientation. An appropriate signal in these amide regions indicates the formation of an oriented alpha-helix.

Figure 6:
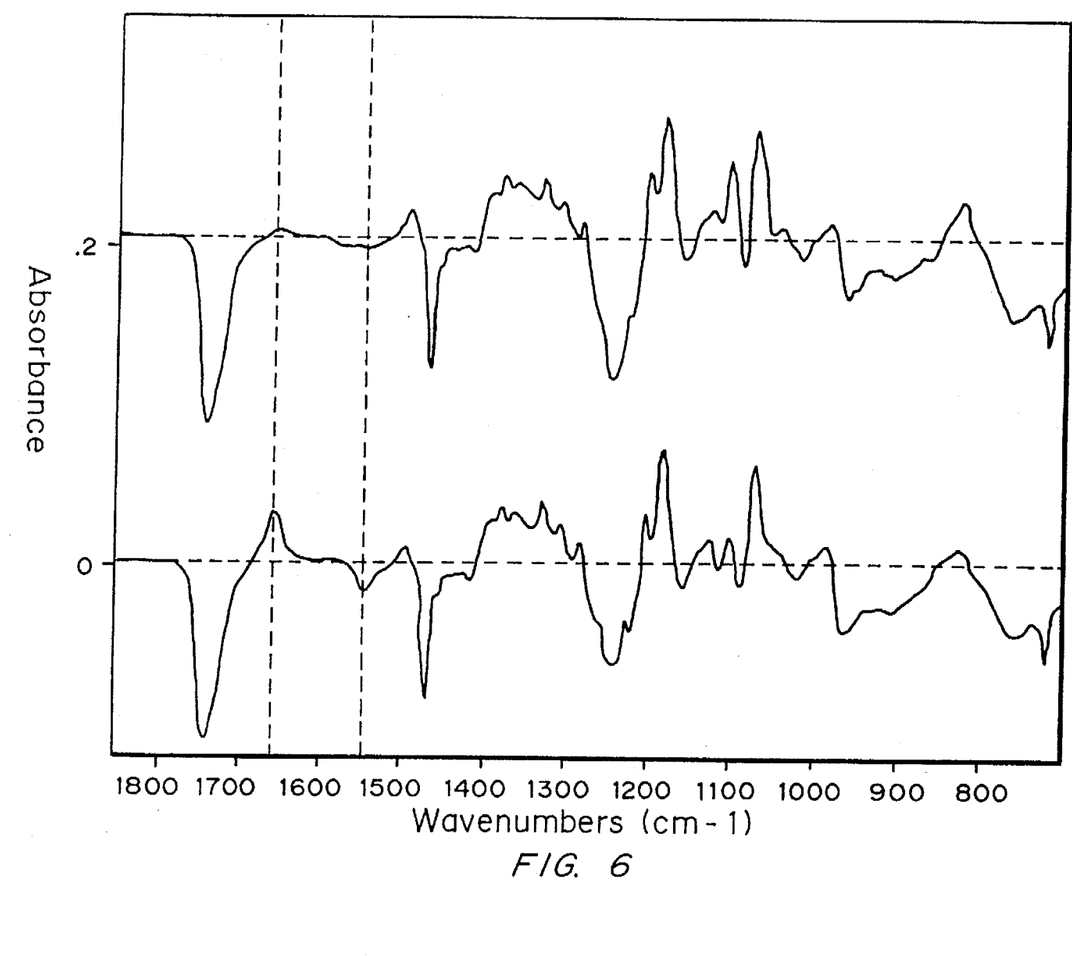
FIG. 6 is a graph showing polarized Fourier Transform Infrared (FTIR) analysis of the synthetic polypeptide of FIG. 1 at basic and acidic pH with the sample tilted at 45 degrees relative to the incident beam. The upper portion of the graph is the synthetic polypeptide deposited at pH 9.2. The lower portion of the graph is the synthetic polypeptide deposited after the addition of 650 nanomoles of HCl in situ. The spectral regions corresponding to the vibrations of the peptide bond are designated by vertical lines.

FIG. 6 shows two difference spectra of horizontally polarized light and vertically polarized light with the samples tilted at 45 degrees relative to the incident beam. The synthetic polypeptide set forth in FIG. 1 and identified in the sequence listing as sequence identification number 1 was the sample analyzed in the graph of FIG. 6. The sample was subjected to FTIR analysis at pH 9.2 and at acidic pH after the addition of 650 nanomoles of hydrogen chloride. As shown in FIG. 6, at pH 9.2 no signal was observed in the regions corresponding to the amide residues, demonstrating very little protein orientation. In contrast, at acidic pH a signal was observed indicating that the polypeptide is in an alpha-helical conformation and that the helix is oriented perpendicular to the plane of the membrane.

Insertion into the Membrane

Tryptophan fluorescence studies of a mixture of the preferred synthetic polypeptide with solutions containing small unilamellar phospholipid vesicles made from synthetic dimyristoyl phosphatidylcholine at various pH values can be used to determine the pH at which the polypeptide inserts into the cell membrane.

Figure 7A:
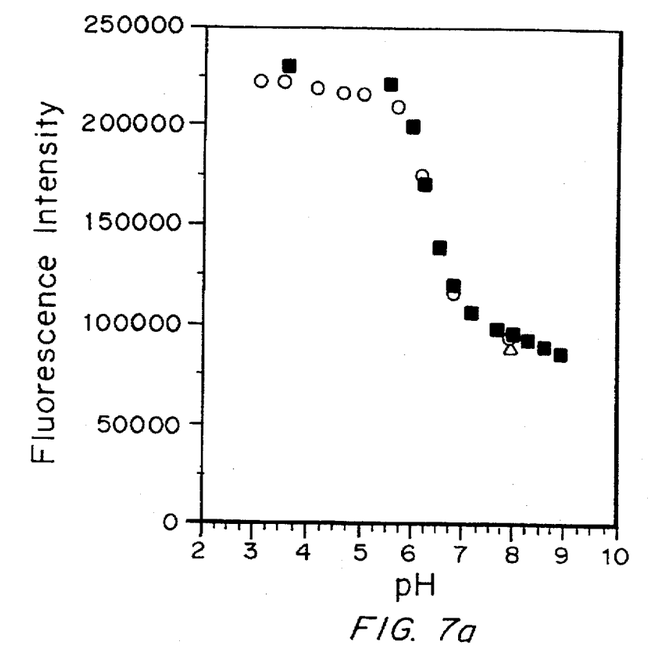
FIG. 7A is a graph showing fluorescence titration of the synthetic polypeptide of FIG. 1 in the presence of dimyristoyl phosphatidylcholine (DMPC) vesicles at various pH values. The black squares indicate the initial titration (up). The open circles indicate the reverse titration (down). The open triangles indicate the second titration (up).
Figure 7B:
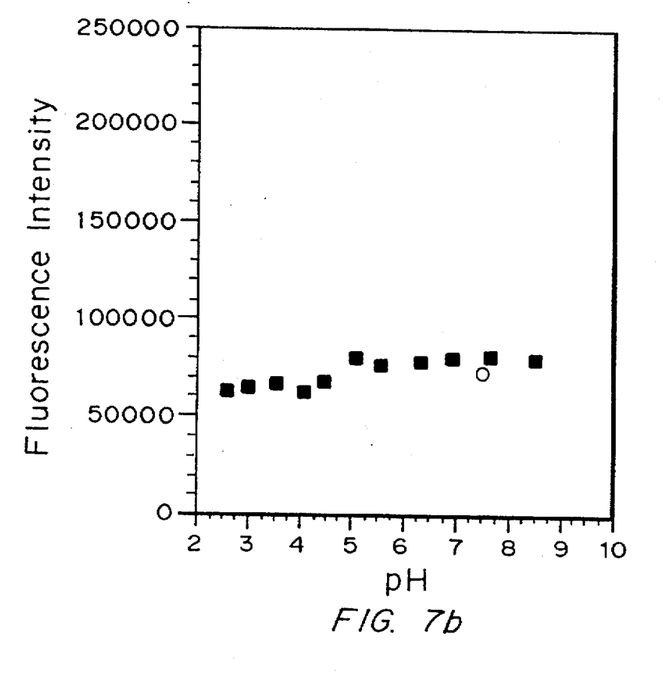
FIG. 7B is a graph showing the circular dichroism analysis of the synthetic polypeptide of FIG. 1 in the presence of lipid molecules. The symbols are the same as set forth in FIG. 7A.

FIG. 7A presents a graph showing fluorescence titration of the synthetic polypeptide shown in FIG. 1 and having the amino acid sequence set forth as sequence identification number 1 in the sequence listing, in the presence of dimyristoyl phosphatidylcholine. The y axis is fluorescence intensity, and the x axis is pH. FIG. 7B is a graph showing fluorescence titration of the polypeptide in the presence of an polar lipids extracted from *H. halobium* as a control.

These studies revealed a transition in the environment of the tryptophan chromophore at approximately pH 6.0. This transition corresponds to insertion of the polypeptide into the membrane and translocation of the helix terminus.

Method of Administration and Concentration

The water-soluble polypeptide is administered by conventional means including intravenously, as a nasal spray, orally, intraperitoneally, intramuscularly, and subcutaneously. The preferred method of administration is intravenously.

The polypeptide is either administered as an aqueous solution or is delivered to the site of action by a liposome or a lipoprotein particle.

An aqueous solution is preferably prepared by first dissolving the polypeptide in a buffer solution containing urea adjusted to a slightly basic pH. The dissolved polypeptide is dialyzed against a buffer to remove the urea.

Most preferably, an aqueous solution is prepared by first dissolving approximately 1 mg/ml of the polypeptide in a buffer solution containing approximately 6 M urea, 200 mM sodium chloride, and 10 mM Tris™ buffer adjusted to a pH of approximately 8.3. All chemicals are available from a commercial chemical supplier such as Sigma (St. Louis, Mo). The dissolved polypeptide is dialyzed against approximately 100 volumes of a buffer solution containing 200 mM sodium chloride and 10 mM Tris, also adjusted to a pH of 8.3. The dialysis solution is changed approximately twice. The polypeptide is then dialyzed against a buffer solution of approximately 20 mM sodium chloride and 5 mM sodium phosphate adjusted to approximately pH 8.0. The dialysis solution is changed approximately three times with 100 volumes of fresh buffer.

Preferably, the aqueous solution contains a polypeptide concentration of between 0.01 and 1 mg/ml. Most preferably, the concentration is 0.03 mg/ml.

The water-soluble hydrophobic polypeptide and method of use described generally above will be further understood with reference to the following non-limiting example.

EXAMPLE

Liposome-mediated Polypeptide Delivery

Delivery of an antiviral agent to an HIV-infected cell is achieved by inserting CD4 molecules in the lipid bilayer of a liposome containing the polypeptide coupled to the antiviral agent by a disulfide bond. The CD4 molecule is the receptor on T lymphocytes to which the HIV glycoprotein 120 (gp120) molecule binds. The polypeptide and HIV-infected cell are brought into proximity by the affinity of gp120 for the CD4 receptor. The antiviral agent is then delivered through the cell membrane into the infected cell by the spontaneously-inserting polypeptide.

Modifications and variations of the water-soluble hydrophobic polypeptide and method of use will be obvious to those skilled in the art from the foregoing description. Such modifications and variations are intended to come within the scope of the appended claims.

---

We claim:

1. An isolated or synthetic polypeptide comprising
a polypeptide derived from a bacteriorhodopsin C molecule,
wherein the polypeptide includes a hydrophobic water-soluble amino acid sequence containing twenty amino acids which forms an alpha-helix capable of spanning the lipid bilayer of a cell and an amino acid which is susceptible to acid or base titration.

2. The polypeptide of claim 1 wherein the titratable amino acid is selected from the group consisting of aspartic acid glutamic acid, lysine, arginine, and histidine.

3. The polypeptide of claim 1 attached to an agent which does not interfer with insertion of the hydrophobic amino acid sequence into the membrane.

4. The polypeptide of claim 1 isolated from a bacteriorhodopsin molecule of *Halobacterium halobium*.

5. The isolated polypeptide of claim 1 comprising the bacteriorhodopsin C peptide.

6. The polypeptide of claim 1 wherein the polypeptide is attached to a ligand molecule that specifically binds to a receptor molecule on the surface of the cell.

7. The polypeptide of claim 1 wherein the polypeptide is inserted within the membrane of a liposome.

8. The polypeptide of claim 7 wherein a ligand molecule, that specifically binds to a receptor molecule on the surface of the cell, is inserted within the membrane of the liposome.

9. The polypeptide of claim 1 wherein the amino acid sequence comprises gly gly glu gln asn pro ile tyr trp ala arg tyr ala asp trp leu phe thr thr pro leu leu leu leu asp leu ala leu leu val asp ala asp xxx gly thr, wherein xxx is selected from the group consisting of glu and gln.

10. The polypeptide of claim 3 wherein the agent is a pharmaceutical compound.

* * * * *

UNITED STATES PATENT AND TRADEMARK OFFICE
CERTIFICATE OF CORRECTION

PATENT NO. : 5,739,273
DATED : April 14, 1998
INVENTOR(S) : Donald M. Engelman, et al.

It is certified that error appears in the above-identified patent and that said Letters Patent is hereby corrected as shown below:

Column 1, line 12, insert the following information:

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Thirteenth Day of April, 1999

*Attest:*

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: internal     ( v i ) ORIGINAL SOURCE:
        ( A ) ORGANISM: Halobacterium halobium     ( x i ) SEQUENCE DESCRIPTION: SEQ ID NO:1:

```
Gly  Gly  Glu  Gln  Asn  Pro  Ile  Tyr  Trp  Ala  Arg  Tyr  Ala  Asp  Trp  Leu
1                   5                        10                       15

Phe  Thr  Thr  Pro  Leu  Leu  Leu  Leu  Asp  Leu  Ala  Leu  Leu  Val  Asp  Ala
               20                       25                       30

Asp  Glu  Gly  Thr
               35
```

( 2 ) INFORMATION FOR SEQ ID NO:2:

( i ) SEQUENCE CHARACTERISTICS:
        ( A ) LENGTH: 248 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: internal     ( v i ) ORIGINAL SOURCE:
        ( A ) ORGANISM: Halobacterium halobium     ( i x ) FEATURE:
        ( A ) NAME/KEY: Region
        ( B ) LOCATION: 10..32
        ( D ) OTHER INFORMATION: /label=Helix A     ( i x ) FEATURE:
        ( A ) NAME/KEY: Region -continued (B) LOCATION: 38..62
            (D) OTHER INFORMATION: /label=Helix B (ix) FEATURE:
            (A) NAME/KEY: Domain
            (B) LOCATION: 72..107
            (D) OTHER INFORMATION: /label=Domain C (ix) FEATURE:
            (A) NAME/KEY: Region
            (B) LOCATION: 80..101
            (D) OTHER INFORMATION: /label=Helix C (ix) FEATURE:
            (A) NAME/KEY: Region
            (B) LOCATION: 108..127
            (D) OTHER INFORMATION: /label=Helix D (ix) FEATURE:
            (A) NAME/KEY: Region
            (B) LOCATION: 136..157
            (D) OTHER INFORMATION: /label=Helix E (ix) FEATURE:
            (A) NAME/KEY: Region
            (B) LOCATION: 167..193
            (D) OTHER INFORMATION: /label=Helix F (ix) FEATURE:
            (A) NAME/KEY: Region
            (B) LOCATION: 203..227
            (D) OTHER INFORMATION: /label=Helix G (xi) SEQUENCE DESCRIPTION: SEQ ID NO:2:

```
Glu Ala Gln Ile Thr Gly Arg Pro Glu Trp Ile Trp Leu Ala Leu Gly
1               5                   10                  15

Thr Ala Leu Met Gly Leu Gly Thr Leu Tyr Phe Leu Val Lys Gly Met
            20                  25                  30

Gly Val Ser Asp Pro Asp Ala Lys Lys Phe Tyr Ala Ile Thr Thr Leu
        35                  40                  45

Val Pro Ala Ile Ala Phe Thr Met Tyr Leu Ser Met Leu Leu Gly Tyr
    50                  55                  60

Gly Leu Thr Met Val Pro Phe Gly Gly Glu Gln Asn Pro Ile Tyr Trp
65                  70                  75                  80

Ala Arg Tyr Ala Asp Trp Leu Phe Thr Thr Pro Leu Leu Leu Leu Asp
                85                  90                  95

Leu Ala Leu Leu Val Asp Ala Asp Gln Gly Thr Ile Leu Ala Leu Val
            100                 105                 110

Gly Ala Asp Gly Ile Met Ile Gly Thr Gly Leu Val Gly Ala Leu Thr
        115                 120                 125

Lys Val Tyr Ser Tyr Arg Phe Val Trp Trp Ala Ile Ser Thr Ala Ala
130                 135                 140

Met Leu Tyr Ile Leu Tyr Val Leu Phe Phe Gly Phe Thr Ser Lys Ala
145                 150                 155                 160

Glu Ser Met Arg Pro Glu Val Ala Ser Thr Phe Lys Val Leu Arg Asn
                165                 170                 175

Val Thr Val Val Leu Trp Ser Ala Tyr Pro Val Val Trp Leu Ile Gly
            180                 185                 190

Ser Glu Gly Ala Gly Ile Val Pro Leu Asn Ile Glu Thr Leu Leu Phe
        195                 200                 205

Met Val Leu Asp Val Ser Ala Lys Val Gly Phe Gly Leu Ile Leu Leu
210                 215                 220
```

-continued

```
Arg  Ser  Arg  Ala  Ile  Phe  Gly  Glu  Ala  Glu  Ala  Pro  Glu  Pro  Ser  Ala
225                      230                 235                           240

Gly  Asp  Gly  Ala  Ala  Ala  Thr  Ser
               245
```